United States Patent
Krill

(10) Patent No.: US 12,017,987 B2
(45) Date of Patent: Jun. 25, 2024

(54) PROCESS FOR ELIMINATING INTERFERING BY-PRODUCTS IN THE DIRECT OXIDATIVE ESTERIFICATION OF METHACROLEIN

(71) Applicant: Röhm GmbH, Darmstadt (DE)

(72) Inventor: Steffen Krill, Muehltal (DE)

(73) Assignee: RÖHM GMBH, Darmstadt (DE)

( * ) Notice: Subject to any disclaimer, the term of this patent is extended or adjusted under 35 U.S.C. 154(b) by 0 days.

(21) Appl. No.: 18/054,109

(22) Filed: Nov. 9, 2022

(65) Prior Publication Data

US 2023/0150912 A1 May 18, 2023

(30) Foreign Application Priority Data

Nov. 12, 2021 (EP) .................................... 21207875

(51) Int. Cl.
 *C07C 67/44* (2006.01)
 *C07C 67/54* (2006.01)
 *C07C 69/54* (2006.01)

(52) U.S. Cl.
 CPC .............. *C07C 67/44* (2013.01); *C07C 67/54* (2013.01); *C07C 69/54* (2013.01)

(58) Field of Classification Search
 CPC ......... C07C 67/44; C07C 67/54; C07C 69/54; C07C 57/58; C07C 67/62
 See application file for complete search history.

(56) References Cited

U.S. PATENT DOCUMENTS

| | | | |
|---|---|---|---|
| 5,969,178 A | 10/1999 | Okamoto et al. | |
| 7,012,039 B2 | 3/2006 | Watanabe et al. | |
| 9,617,199 B2 | 4/2017 | Krill et al. | |
| 9,890,105 B2 | 2/2018 | Krill et al. | |
| 9,963,417 B2 | 5/2018 | Krill et al. | |
| 10,301,251 B2 | 5/2019 | Groemping et al. | |
| 10,596,539 B2 | 3/2020 | Lygin et al. | |
| 10,766,847 B2 | 9/2020 | Krill et al. | |
| 11,124,471 B2 | 9/2021 | Lygin et al. | |
| 11,299,449 B2 | 4/2022 | Krill et al. | |
| 11,427,664 B2 | 8/2022 | Krill et al. | |
| 11,472,762 B2 | 10/2022 | Krill et al. | |
| 2016/0200660 A1* | 7/2016 | Krill | C07C 67/54 560/208 |

(Continued)

FOREIGN PATENT DOCUMENTS

| | | |
|---|---|---|
| EP | 3 450 422 | 3/2019 |
| EP | 3 350 153 | 6/2019 |
| WO | 2014/170223 | 10/2014 |

OTHER PUBLICATIONS

U.S. Pat. No. 9,617,199, Apr. 11, 2017, 2016/0251301, Krill et al.

(Continued)

*Primary Examiner* — Jafar F Parsa
(74) *Attorney, Agent, or Firm* — Grüneberg and Myers PLLC

(57) ABSTRACT

A process can be used for preparing methyl methacrylate (MMA), by direct oxidative esterification of methacrolein. The MMA and polymers produced therefrom feature a very low yellowness index. A workup of the reactor output from the oxidative esterification of methacrolein allows for particularly discolouring by-products to be removed or degraded without significant MMA losses.

19 Claims, 1 Drawing Sheet

(56) References Cited

U.S. PATENT DOCUMENTS

| | | |
|---|---|---|
| 2016/0251301 A1 | 9/2016 | Krill et al. |
| 2016/0280628 A1 | 9/2016 | Krill et al. |
| 2019/0099731 A1 | 4/2019 | Lygin et al. |
| 2021/0032386 A1 | 2/2021 | Krill et al. |
| 2021/0047259 A1 | 2/2021 | Lygin et al. |
| 2021/0047261 A1* | 2/2021 | Saito ................. B01D 3/34 |
| 2021/0269385 A1 | 9/2021 | Krill et al. |
| 2022/0204436 A1 | 6/2022 | Krill et al. |

OTHER PUBLICATIONS

U.S. Pat. No. 9,963,417, May 8, 2018, 2016/0280628, Krill et al.
U.S. Pat. No. 10,596,539, Mar. 24, 2020, 2019/0099731, Lygin et al.
U.S. Pat. No. 11,124,471, Sep. 21, 2021, 2021/0047259, Lygin et al.
U.S. Pat. No. 11,427,664, Aug. 30, 2022, 2021/0032386, Krill et al.
U.S. Appl. No. 17/814,490, filed Jul. 22, 2022, Krill et al.
U.S. Pat. No. 11,299,449, Apr. 12, 2022, 2021/0269385, Krill et al.
U.S. Pat. No. 11,472,762, Oct. 18, 2022, 2022/0204436, Krill et al.
U.S. Appl. No. 17/753,245, filed Feb. 24, 2022, Steffen Krill.
U.S. Appl. No. 17/804,057, filed May 25, 2022, Krill et al.

* cited by examiner

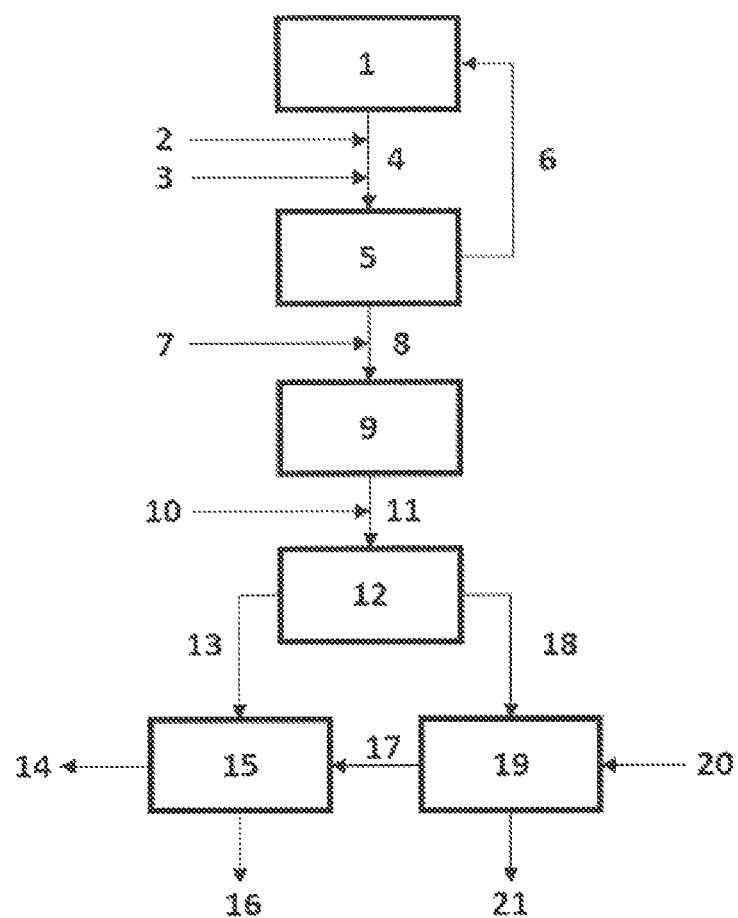

PROCESS FOR ELIMINATING INTERFERING BY-PRODUCTS IN THE DIRECT OXIDATIVE ESTERIFICATION OF METHACROLEIN

CROSS-REFERENCE TO RELATED APPLICATIONS

This application claims priority to European Application No. 21207875.2, filed on Nov. 12, 2021, the content of which is hereby incorporated by reference in its entirety.

BACKGROUND OF THE INVENTION

Field of the Invention

The present invention relates to a process for preparing methyl methacrylate, where this MMA and polymers produced therefrom feature a very low yellowness index. The MMA is in this case prepared according to the invention by direct oxidative esterification of methacrolein.

In particular the present invention relates to a workup of the reactor output from the oxidative esterification of methacrolein, by means of which particularly discolouring by-products are removed or degraded without significant MMA losses.

Description of Related Art

Methyl methacrylate is used in large amounts for preparing polymers and copolymers with other polymerizable compounds. In addition, methyl methacrylate is an important synthesis unit for a variety of specialty esters based on methacrylic acid (MAA) which can be prepared by transesterification with the appropriate alcohol. There is consequently a great interest in very simple, economical and environmentally friendly processes for preparing this starting material. Of particular interest here is the provision of methyl methacrylate (MMA) or other alkyl methacrylates, which result in low yellow discolouration during the polymerization.

MMA is prepared nowadays by a variety of processes proceeding from $C_2$, $C_3$ or $C_4$ synthesis units. In one process which is said to be particularly efficient, MMA is obtained by gas-phase oxidation of isobutylene or tert-butanol with atmospheric oxygen over a heterogeneous catalyst to afford methacrolein and subsequent oxidative esterification reaction of methacrolein using methanol. This process, developed by ASAHI, is described, inter alia, in publications U.S. Pat. Nos. 5,969,178 and 7,012,039. A particular disadvantage of this process is a very high energy requirement. In a development of the process, the methacrolein is obtained from propanal and formaldehyde in the first stage. Such a process is described in WO 2014/170223.

U.S. Pat. No. 5,969,178 describes such a process for oxidative conversion of isobutene or tert-butanol to methacrolein and subsequent oxidative esterification to MMA. In this second stage, a liquid mixture of methacrolein and methanol with reduced water content is reacted with molecular oxygen and a palladium catalyst, wherein said catalyst is usually in supported form as a palladium-lead catalyst. In a first distillation stage, a mixture of methacrolein and methanol is then removed from the crude product of the oxidative esterification as overhead condensate of a rectifying column, while low-boiling constituents, for example comprising acetone, are removed overhead as vapour. The MMA-containing and methacrolein-poor bottoms are then passed into a second distillation stage, with a saturated hydrocarbon, which for example is selected from hexane, heptane, octane and isomers thereof, being added to the tops reflux of this second distillation stage. This saturated hydrocarbon forms an azeotrope with the methanol in the second distillation stage—for example the methanol/n-hexane azeotrope having a boiling point at 49.9° C.—as a result of which the methanol is separated from the MMA-containing phase, which remains in the bottom. In addition, water also forms an azeotrope with the saturated hydrocarbon, such as for example the water/n-hexane azeotrope having a boiling point at 61.6° C. and is likewise separated from the MMA. In the bottom of the distillation column remains a crude MMA which, in addition to the MMA, also contains further high boiler products such as for example methacrylic acid. At the top of the second distillation stage, the two azeotropes of methanol and water respectively with the saturated hydrocarbon are condensed and passed into a phase separator. If required, fresh, saturated hydrocarbon may be added in the form of a "make up" to this condensate stream. The upper phase in the phase separator mainly contains the saturated hydrocarbon, and is returned to the second distillation stage as reflux. The lower phase in the phase separator is passed into a third distillation stage, where a mixture of methanol and water is obtained as bottom product. This mixture can be supplied to a dewatering operation between the isobutene or tert-butanol oxidation to give methacrolein and the actual direct oxidative esterification, which reduces the amount of water in the direct oxidative esterification.

The overhead product of the third distillation stage consists of the two azeotropes of methanol and water respectively with the saturated hydrocarbon used, and is recycled into the phase separator in condensed form.

The reactants of the direct oxidative esterification are thus directly or indirectly recycled and the crude MMA can ultimately be purified to commercial quality.

The document U.S. Pat. No. 5,969,178 discloses a further alternative embodiment for recycling the reactants. Here, the reaction product from the direct oxidative esterification is passed into a first distillation column, with the feed to the column being situated approximately in the middle of the column. The overhead condensate obtained in this distillation column is a mixture, inter alia, of methanol, methacrolein, MMA and water. Vapours removed overhead may, as previously, be low-boiling constituents that for example contain acetone. The overhead condensate is a consequence of the two azeotropes, of methacrolein and methanol having a boiling point of 58.0° C. and of MMA and methanol having a boiling point of 64.5° C. Analogously to the preceding embodiment, this overhead distillate can then be supplied to the dewatering between the isobutene or tert-butyl oxidation to give methacrolein and the actual direct oxidative esterification; however, in this case the MMA must be recovered separately from the bottom product of the dewatering, since otherwise the yield of methacrylic product decreases.

The bottom product of the first distillation column contains, in addition to MMA, water and high boiler products, such as for example methacrylic acid. This bottom product is phase-separated after cooling and the organic, MMA-containing phase is subjected to a conventional workup to remove high and low boiler products, in order to obtain a commercial grade MMA quality. The aqueous phase is discarded, which results in a loss of yield in the form of MMA and methacrylic acid dissolved in water.

U.S. Pat. No. 7,012,039 discloses a slightly different workup of the reactor output from the oxidative esterification. In a first distillation stage, methacrolein is distilled off overhead via sieve trays and the aqueous, MMA-containing mixture is passed from the column bottom into a phase separator. In said phase separator, the mixture is adjusted to a pH of about 2 by addition of sulfuric acid. The separation of the sulfuric-acid-treated water from the organic/oil phase is then effected by means of centrifugation. This oil phase is separated in a further distillation into high-boiling constituents and an MMA-containing phase which is withdrawn overhead. The MMA-containing phase is then separated from low-boiling constituents in a third distillation. This is followed by yet a fourth distillation for final purification.

The problem with this process is the sulfuric acid, which needs to be added in large amounts and can have corrosive effects on parts of the plant. Accordingly, these parts, such as the phase separator (which is described as centrifuge) or else the second distillation column in particular, have to be fabricated from suitable materials. Moreover, U.S. Pat. No. 7,012,039 is silent regarding the handling of the simultaneously generated methacrylic acid or the residual methanol remaining in the product. However, it can be assumed that the former is also removed in the distillation stages, while the methanol can only partly be obtained and returned with the methacrolein, while the remainder is probably lost in the third distillation stage. The process per se is problematic with respect to the preparation of on-spec and colourless MMA, especially as a result of the oxidation of isobutene to give methacrolein as first process step, since here significant proportions of diacetyl are produced in the gas phase; diacetyl is a known yellow colour-imparting substance for MMA and PMMA produced therefrom and its trace concentration must be painstakingly controlled. Furthermore, the prior art contains no indication of the amounts in which acetals of methacrolein, in particular methacrolein dimethyl acetal, are formed, or how these are physically or chemically treated and removed in the process. It should be pointed out that the addition of sulfuric acid in this patent serves in particular for the removal of lead cations in the form of sparingly soluble lead sulfate, in order to obtain a wastewater that satisfies the requirements for municipal clear waters. The lead cations are dissolved out from the catalyst of the second stage, and in order to maintain catalyst activity lead acetate must additionally be continuously supplied to the second stage.

WO 2014/170223 describes a similar process to U.S. Pat. No. 7,012,039. The only difference is that in the actual reaction the pH is adjusted in a circuit by addition of a methanolic sodium hydroxide solution. This serves, inter alia, to protect the catalyst. Moreover, the removal of the aqueous phase in the phase separation is simpler on account of the salt content. However, another consequence is that the methacrylic acid formed is in the form of sodium salt and is later removed and discarded with the aqueous phase. In the variant with an addition of sulfuric acid in the phase separation, the free acid is indeed recovered. However, in doing so sodium (hydrogen)sulfate is formed which can lead to other problems during disposal.

Lastly, EP 33 501 53 B1 (WO 2017/046110) teaches an optimized workup of the crude MMA obtained from an oxidative esterification, in which the crude MMA is initially separated from a heavy phase and subsequently distilled off from this heavy phase is an alcohol-containing light phase which in turn can be recycled. The particular feature of this process is moreover that here the methacrolein has been obtained on the basis of propanal and formaldehyde, wherein the former is obtained on the basis of C2 synthesis units, for example from ethylene and synthesis gas. The patent teaches the workup of MMA-containing product mixture from a direct oxidative esterification of methacrolein and methanol to give MMA by withdrawing unconverted reactants, methacrolein and methanol, by distillation overhead in a first distillation column and recycling them into the reactor of the direct oxidative esterification. The mixture of MMA, water and methanol obtained in the bottom additionally contains free methacrylic acid and also the corresponding alkali metal salt, as well as small proportions of methacrolein dimethyl acetal. This mixture is acidified and admixed with additional water. A phase separation is then effected in a phase separator, followed by extraction of the organic upper phase. It is mentioned in this sequence of workup steps that the corresponding acetal is also cleaved. However, no indications are given concerning the completeness of the acetal cleavage, and it is left open as to how the cleavage products methacrolein and methanol are directly or indirectly worked up. This teaching also leaves it open as to how much of the acetal remains in the final pure MMA, and what effect this has on the product quality for applications.

However, independently of the raw material basis for the methacrolein used, all of these processes result overall in MMA or in general alkyl methacrylates that result in yellow discolouration, in particular of descendent products, for example PMMA molding compounds. There is thus a need for improvement of the kind where the source of this yellow discolouration prior to the polymerization is removed from the relevant alkyl methacrylate, in particular MMA, as efficiently as possible.

In EP 34 504 22 A1, two different substances were identified as relevant for this yellow discolouration of the descendant products of an MMA prepared by means of direct oxidative esterification. Primarily, this is a methacrolein dimethyl acetal (hereinafter also referred to as DMIB). Furthermore, methyl isobutyrate formed as a by-product in the process also appears to play a role in the discolouration. The concept was then proposed of further converting the reactor output from the oxidative esterification in a further reactor with reduced alcohol content, increased water content and lower pH. However, this method requires an additional reaction apparatus. Furthermore, this reactor needs to be of relatively large design in order to achieve a residence time that is sufficient for appreciable reduction of the by-products. The patent application teaches the treatment of a product mixture from the direct oxidative esterification, wherein first unconverted methacrolein and methanol are removed by distillation and the remaining bottom fraction, containing MMA, water, methanol, free methacrylic acid and the corresponding alkali metal salt and small proportions of methacrolein dimethyl acetal, are brought into contact with additional water and acid in an additional reactor, resulting the achievement of extensive hydrolysis of the acetal. The acetal hydrolysis and the hydrolysis of methyl isobutyrate are described in a variety of embodiments, for instance a continuous stirred tank, a plug flow reactor, a phase separator, or a column bottom. While the hydrolysis of the acetal and the methyl isobutyrate does proceed efficiently and an acetal content of less than 20 ppm is achieved, the application does not explicitly mention that the hydrolysis of MMA, and hence the product of value of the process, also takes place under the conditions described. The yield of the target product thus decreases and there is formation of additional methacrylic acid and also the addition product of water or methanol onto the conjugated double bond. The formation of hydroxyisobutyric acid is critical in particular, since this component has a strongly corrosive action.

SUMMARY OF THE INVENTION

Problem

In view of the prior art, one problem addressed by the present invention is accordingly that of providing a technically improved process for oxidative esterification of methacrolein to prepare MMA which when processed further results in a particularly low yellow discolouration of the descendant products.

A further problem addressed by the present invention was in particular that of efficiently removing from the MMA the by-product DMIB formed during the oxidative esterification of methacrolein and leading in particular to the yellow discolouration of the descendant products.

Furthermore, a problem to be solved is also that of minimizing the content of the further byproduct methyl isobutyrate in the final MMA.

An additional problem was that of avoiding by-products leading to yellow discolouration in such a way as to minimize the loss of MMA, especially for example in the form of hydrolysis of MMA to methacrylic acid.

A further problem was that of providing a process that can be performed with a minimum disposal cost, in particular through reduced generation of organic constituents and acids in the waste stream.

Solution

These problems were solved by the development of a novel process for preparing an alkyl methacrylate, especially alkyl MMA. This process comprises the following process steps:
a. preparing methacrolein in a reactor I,
b. oxidatively esterifying the methacrolein in the presence of an alcohol, oxygen and a heterogeneous noble metal-containing catalyst in at least one reactor II
c. distilling the reactor output from reactor II in a distillation column I for separation of methacrolein and portions of the methanol,
d. optionally pretreating the bottom output from process step c, comprising the steps of
   i. adding an acid to change the pH,
   ii. adding water to obtain a biphasic mixture and
   iii. reactively treating at least a portion of the mixture from ii, and
e. extracting the bottoms from distillation column I or at least one organic phase of the bottom output from distillation column I in an extraction I.

The invention also includes the following embodiments:
1. Process for preparing alkyl methacrylates, comprising the process steps of
   a. preparing methacrolein in a reactor I,
   b. oxidatively esterifying the methacrolein in the presence of an alcohol, oxygen and a heterogeneous noble metal-containing catalyst in at least one reactor II
   c. distilling the reactor output from reactor II in a distillation column I for separation of methacrolein and portions of the methanol,
   d. optionally pretreating the bottom output from process step c, comprising the steps of
      i. adding an acid to change the pH,
      ii. adding water to obtain a biphasic mixture and
      iii. reactively treating at least a portion of the mixture from ii, and
   e. extracting the bottoms from distillation column I or an organic phase of the bottom output from distillation column I in an extraction I.
   characterized in that the amount of the methacrolein in the organic output from extraction I is greater than that in the bottom output from distillation column I.
2. Process according to embodiment 1 for preparing alkyl methacrylates, comprising a process step e., which is an extraction of the bottoms from distillation column I in an extraction I, characterized in that extraction I and optionally distillation column I are designed to be acid-resistant, in that an organic and/or a mineral acid is mixed with the reactor stream from reactor II, and is passed into the distillation column I and/or the extraction I, in that the reactor output has an average residence time in distillation column I of between 1 and 30 min at a temperature of between 30 and 100° C., and in that in extraction I the bottoms transferred from distillation column I with the additionally transferred acid resides in the extraction at a temperature of between 10 and 100° C. for 1 to 20 min.
3. Process according to embodiment 1 or 2, characterized in that the reaction in reactor II is effected at a water content of between 0.1% and 10% by weight and a pH of between 5 and 8.
4. Process according to at least one of embodiments 1 to 3, characterized in that process step a in reactor I involves the reaction of propanal with formaldehyde in the presence of at least one acid and optionally an amine, and in that the alcohol in process step b is methanol and the alkyl methacrylate is MMA.
5. Process according to at least one of embodiments 1 to 4, characterized in that in process step c methacrolein dimethyl acetal is cleaved with water into methacrolein and methanol, which in distillation column I together with the remaining reactants of process step b, are largely removed overhead or in a side stream of the distillation column I and are recycled into reactor II.
6. Process according to at least one of embodiments 1 to 5, characterized in that in process step c sulfuric acid is passed as said acid into the distillation column I and optionally additionally in process step e into the extraction.
7. Process according to at least one of embodiments 1 to 6, characterized in that additional water is introduced into the bottom of distillation column I. and in that the distillation is effected at a bottom temperature of between 50 and 100° C.
8. Process according to at least one of embodiments 1 to 7, characterized in that the extraction I involves a mixer-settler, and in that the extractant used is water, aqueous sulfuric acid or the bottom stream from distillation column IV.
9. Process according to at least one of embodiments 1 to 8, characterized in that the acid is added to the stream departing from the bottom of distillation column I.
10. Process according to at least one of embodiments 1 to 9, characterized in that process step e. is followed by isolation and purification stages, which are at least one optional phase separator, at least one high boiler column and at least one low boiler column.
11. Process according to embodiment 10, characterized in that in process step d. in the extraction I the bottom output from distillation column I is separated into an MMA-containing phase and a polar phase containing the acid used and salts thereof, in that the MMA-containing phase is subsequently passed into a distillation column II, which is preferably a distillation column for separating high-boiling constituents from the MMA phase.

12. Process according to embodiment 11, characterized in that the distillation column II is of acid-resistant design, and in that an acid, preferably sulfuric acid, is introduced into the bottom and/or the feed of distillation column II.

13. Process according to embodiment 11, characterized in that the distillation column II is a distillation column for separating low-boiling constituents from the MMA phase, into the bottom and/or feed of which an acid, preferably sulfuric acid, is introduced, and in that the bottoms of this distillation column II are passed into an acid-resistant distillation column III for separating high-boiling constituents from the MMA phase.

14. Process according to at least one of embodiments 1 to 13, characterized in that the acid added has a pKa value which is 1 less than that of methacrylic acid.

15. MMA, preparable by means of process steps a to d of a process according to at least one of embodiments 1 to 11, characterized in that the MMA comprises methacrolein dimethyl acetal DMIB and methyl isobutyrate and has a DMIB content of less than 90 ppm and a methyl isobutyrate content of less than 200 ppm.

16. MMA according to embodiment 15, characterized in that the MMA has a content of DMIB of less than 50 ppm and a methyl isobutyrate content of less than 250 ppm.

BRIEF DESCRIPTION OF THE DRAWING

The FIGURE shows an embodiment of part of the process according to the invention.

DETAILED DESCRIPTION OF THE INVENTION

The invention is in particular characterized in that the amount of the methacrolein in the organic output from extraction I is greater than the amount of the methacrolein in the bottom output from distillation column I. This is achieved according to the invention in particular by the hydrolytic conversion of methacrolein-based acetals and hemiacetals. This is achieved in turn preferably by conducting the reaction by means of a reactive distillation and/or reactive extraction.

The invention is additionally characterized in that the methacrylic acid amount in the organic output from extraction I differs from the amount of methacrylic acid in the bottom output from distillation column I by less than 10% and preferably less than 5%, this being based on the methacrylic acid and salts thereof in the bottom output from distillation column I. This is achieved by the combination of acetal cleavage in a reactor, provided for this purpose, with an extraction apparatus in which hydrolysis also takes place.

The direct oxidative esterification of methacrolein to give MMA proceeds according to the prior art with a selectivity for MMA of greater than 90%; in addition, depending on the conditions such as for instance the water content in the direct oxidative esterification, a selectivity for methacrylic acid of between 1% and 5% is achieved, and a selectivity for methyl 3-methoxyisobutyrate of between 0.5% and 3% is also found. The process according to the invention surprisingly enables hydrolysis of the DMIB of more than 90%, while simultaneously reducing the undesired hydrolysis of the MMA to methacrylic acid to a hydrolysis conversion of less than 3%. The undesired hydrolysis can preferably be reduced to a conversion of less than 1%, very particular preferably to a conversion of less than 0.5%.

The process according to the invention is preferably characterized in that distillation column I and extraction I are each designed to be acid-resistant, and in that an organic and/or a mineral acid is passed into the reactor stream from reactor II and/or into the bottom of distillation column I.

Preferably, this added acid has a pKa value which is 1 less than, preferably 2 less than, that of methacrylic acid.

In a first embodiment of the invention, the bottom output from distillation column I is passed in its entirety into extraction I, preferably into the bottom of extraction I. The acid is preferably added, to release methacrylic acid from the alkaline earth metal/alkali metal methacrylate, either already in the distillation column I or in the bottom stream departing from distillation column I.

In a second, alternative embodiment of the present invention, the bottom output from distillation column I is first passed into a phase separator I in which a separation is effected into an organic, methacrolein-rich phase, which in particular is a phase consisting predominantly of MMA, and a polar, water-rich phase. The phase separation is facilitated by the addition of water and the addition of an acid, whereupon the bottom output from the distillation column undergoes a pH change. In this embodiment, the organic phase is then passed into the extraction I, while the polar phase is transferred into a distillation column IV. Alcohol fractions, especially methanol fractions, can be separated from the aqueous phase in this distillation column IV. The alcohol-containing top fraction can then be directly or indirectly recycled into reactor II, while the aqueous bottom fraction can be disposed of. The bottom fraction from extraction I may in addition be passed into this distillation column IV in order to improve the overall raw material consumption.

In a variant I of the first embodiment, between distillation column I and extraction I there is located a reactor III, in which the bottom output from distillation column I is thermally treated while adding water, before being passed into the extraction I. This reactor III has the task of effecting hydrolytic cleavage of methacrolein-containing acetals and hemiacetals.

In a variant II of the second embodiment, between distillation column I and phase separator I there is located such a reactor III, in which the bottom output from distillation column I is thermally treated while adding water. This reactor III has the task of effecting hydrolytic cleavage of methacrolein-containing acetals and hemiacetals.

In all four embodiments or variants, the acid can be supplied to the bottom stream from distillation column I already before the introduction into extraction I. In variant I or II, this is done for example upstream of reactor III or directly into reactor III. Preference is given in the second embodiment to passing the acid upstream of phase separator I and/or directly into extraction I. This effectively brings about the release of methacrylic acid from the respective alkaline earth metal/alkali metal methacrylate and at the same time the formation of the corresponding salt pair. When using sulfuric acid and sodium methacrylate, sodium (hydrogen)sulfate is for example formed as corresponding salt pair.

In the above-described embodiments or variants, the acid is particularly preferably added upstream of phase separator I and optionally upstream of reactor III. The addition of the acid at these described positions has the advantage that the alkaline earth metal/alkali metal salts from reactor II are preformed and are present predominantly in the polar phase, as a result of which the subsequent phase separation and the extraction I proceed more efficiently. Within these embodiments or variants, it is also conceivable to add the acid at more than one position.

Furthermore, in the process according to the invention the reactor output in distillation column I preferably has an average residence time of between 1 and 30 min, in particular between 1 and 20 min, at a temperature of between 30 and 100° C. Moreover, the bottoms transferred from distillation column I with the additionally transferred acid resides in the extraction I at a temperature of between 10 and 100° C., preferably not more than 90° C., and particularly preferably between 20 and 60° C., for 1 to 20 min.

In the process according to the invention, the reactor III preferably also has an average residence time of between 10 seconds and 30 minutes, in particular between 1 and 5 minutes, at a temperature of between 20 and 100° C., with the reaction mixture in the reactor III preferably being subjected to turbulent mixing.

There are in particular a plurality of alternatives as regards the feed of the reactor stream from reactor II which is mixed with an organic and/or mineral acid. It is also possible, if less preferred, to pass the acid directly into distillation column I, the latter in this embodiment then necessarily being of acid-resistant design. Alternatively, the mixture may also be mixed with another stream upstream of the feed into distillation column I. In addition, the stream may also be sent into the extraction I or mixed beforehand with another stream upstream of the feed into extraction I. The acid may alternatively also be fed into the feed of the reactor III or directly into the reactor III. It is also possible, although not preferred, for the acid and the reactor output to be passed separately into distillation column I or into extraction I.

It should be noted that the individual process steps need not be performed in continuous immediately consecutive fashion. Further process steps, for example intermediate purifications, may also be performed in particular between the recited steps a and b. Process steps a to e, optionally supplemented by intermediate steps, are effected consecutively in the specified sequence and in continuous operation. In general, and preferably, steps b to d are effected without such intermediate steps, while the methacrolein (MAL) from process step a. is first purified and dewatered before being used in process step b.

The reaction in reactor II is preferably effected at a water content of between 0.1% and 10% by weight and a pH of between 5 and 8.

In principle, the methacrolein in process step a. in reactor I may be prepared on the basis of C2 or C4 synthesis units. It is preferable for process step a to be the reaction of propanal with formaldehyde in the presence of at least one acid and optionally an amine, i.e. a process step proceeding from C2 synthesis units. In particular, the process according to the invention may be applied to the combinations of such a C2-based process for preparing methacrolein and a subsequent oxidative esterification to afford an alkyl methacrylate in process step b. This relates in particular to the descriptions of such a combination of process steps a and b as may be found for example in DE 3 213 681, U.S. Pat. No. 4,408,079, CN 1 038 461 04 or EP 3 194 355.

Process step a in reactor I is preferably the reaction of propanal with formaldehyde in the presence of at least one acid and optionally an amine. The propanal is particularly preferably additionally obtained from a C2 process. According to the invention the "C2 process" is to be understood as meaning processes which proceed from a C2 synthesis unit in the synthesis of an alkyl methacrylate. In the context of the present invention, it is particularly preferable in addition for the propanal for process step a) to be obtained on the basis of ethylene and synthesis gas.

It is also preferable for the alcohol in process step b to be methanol and for the alkyl methacrylate to be MMA.

As a result of the addition of the acid, methacrolein dimethyl acetal (dimethoxyisobutene, DMIB) is cleaved with water into methacrolein and methanol in process steps d and e, or in variant I or II in reactor III and in process steps d and e. These cleavage products correspond to the reactants used in process step b and together with these remaining reactants are largely removed overhead or in a side stream of the distillation column I and/or extraction I and/or optional distillation column IV and optionally recycled directly or indirectly into reactor II. The wording "largely" this case generally encompasses at least 70% of the MAL and of the methanol. If the recycling rate is subtracted from the output of reactor II, then this is preferably even above 98% for MAL and methanol.

Alternatively, the overhead product of extraction I may also be separated by distillation into an MMA-containing phase and a low boiler phase, the reactants from process step b being in the low boiler phase. This low boiler phase is in turn composed of an organic and an aqueous phase. Fractions of the aqueous phase and/or of the organic phase contain components that are difficult to separate from MMA, such as for example methyl isobutyrate or methyl propionate, and may therefore optionally be discharged from the process instead of being recycled in full into the process.

The acid may be added in process step d in such a way that it is passed directly into the bottom of distillation column I. Alternatively, or less preferably, the acid may however additionally also be supplied to the feed from, for example, reactor II. It is also possible for the crude product from reactor II to first be provided with the acid in a mixing chamber before this mixture is fed into distillation column I.

When adding the acid to the bottom of the column, the combination of column design and choice of the acid should be taken into account. In particular in the case where the column is filled to a relevant extent with distillation packings, an acid should not be chosen that forms a sparingly soluble salt with any ions that might potentially be present, such as sodium ions. In order to prevent an associated blocking or clogging of the column over time, it is possible if acid is being added to the column bottom to for example use methanesulfonic acid instead of sulfuric acid.

The acid used is particularly preferably sulfuric acid. Sulfuric acid here includes concentrated sulfuric acid, but also aqueous solutions of sulfuric acid. Preference is given to using an aqueous sulfuric acid with a sulfuric acid content of at least 10% by weight. The distillation in distillation column I is further preferably effected at a bottom temperature of between 50 and 100° C. This internal temperature, measured in the liquid phase, depends here in particular on the internal pressure and on the precise configuration of the distillation column used. Columns having intermediate trays, packing material or relatively large internal volume can generally be operated at different temperatures from columns not having the respective arrangements.

Optionally, additional water may be introduced into the bottom of distillation column I in order to improve results.

Particular preference is given to adding the acid to the stream departing from the bottom of distillation column I.

In an optional embodiment of the present invention, the acid, preferably sulfuric acid, can be additionally passed in process step e into the extraction, where the sulfuric acid may be concentrated, but aqueous solutions of sulfuric acid may also be used; preference is given to using an aqueous sulfuric acid having a sulfuric acid content of at least 10% by weight. Depending on the configuration of the overall process, this additional acid in the extraction can bring about a further reduction in the by-product content, in particular of DMIB. Those skilled in the art can readily ascertain, with few modifications, whether an additional acid addition into extraction I will have a positive effect in the selected embodiment, or whether the acid transferred from process step d will be sufficient in extraction I. Irrespective of this, process step e can be considered to be a reactive extraction. The cleavage of the methacrolein-containing acetals by means of water in acidic medium is conducted by means of the process according to the invention in such a way that after isolation MMA of a commercial quality can be obtained having DMIB contents of less than 90 ppm.

The extraction I in process step d preferably involves a mixer-settler. However, alternatively, other apparatuses may also be used, such as for example a centrifugal extraction or stirred cell extraction. The combination of a plug flow reactor as reactor III and a settler as phase separator I upstream of extraction I has also proven to be very favourable. Optionally, additional water can also be supplied in one of these variants.

The medium used as extractant is preferably water, aqueous sulfuric acid or at least portions of the bottom stream from distillation column IV.

Process step e is generally followed by isolation and purification stages. These purification stages may be phase separators, distillation columns such as high and low boiler columns, or crystallization chambers. They are preferably optionally at least one phase separator, at least one high boiler column and at least one low boiler column.

In process step e in the extraction I the bottom output from distillation column I is separated into an alkyl methacrylate-containing, especially MMA-containing, phase and a polar phase containing the acid used and salts thereof. Methacrylic acid formed or other light organic acids may in contrast by all means predominantly remain in the MMA-containing phase. The MMA-containing phase is preferably then passed into a distillation column II. This distillation column II is preferably a distillation column for separating high-boiling constituents from the MMA phase.

This distillation column II is preferably of acid-resistant design.

In an alternative embodiment, distillation column II is preferably a distillation column for separating low-boiling constituents from the MMA phase. In this case, an acid, preferably sulfuric acid and especially aqueous sulfuric acid, can be introduced into the bottom and/or feed of said column. In this embodiment, the bottoms of this distillation column II are then passed into an acid-resistant distillation column III for separating high-boiling constituents from the MMA phase, meaning that in this particular embodiment the MMA-containing stream is brought into contact with the acid at a relatively high temperature in a total of four different process steps, with the by-product proportion being reduced each time.

However, very particular preference is given to a further embodiment, which compared to the preceding one is of inverse design, and in which distillation column II is a high boiler column and distillation column III is a low boiler column. In this embodiment, in general no acid is added into distillation column III.

According to the invention, the present invention has the particular feature that in process step c in the bottom of distillation column I the water content is at least 2% by weight, preferably at least 3% by weight, and especially preferably at least 4% by weight higher in absolute terms than in reactor II. In some embodiments of the present invention, in particular when the acid is sent directly into the bottom of extraction I, the water content difference may also by all means be 20% by weight or even more than 30% by weight higher in absolute terms than in reactor II.

In addition, the alcohol concentration in process step c in the bottom of distillation column I is lower than in reactor II, in which process step b is conducted. Although this already results from the distillation alone, it does appear to play a decisive role with respect to the decomposition of the DMIB.

Lastly, this novel process is characterized in that the pH in the bottoms discharge from distillation column I after addition of the acid is generally between 0.5 and 7, preferably between 0.5 and 4, especially between 0.5 and 3, and is at least 0.5 lower than is established in reactor II.

The pH values in the extraction I are generally between 0.5 and 7 after addition of the acid. The acid here can be added according to embodiments 1 and 2 and variants I and II thereof. The pH is preferably between 0.5 and 4, especially between 0.5 and 3 and is preferably at least 0.5 lower than in reactor II.

It has surprisingly been found that the alkyl methacrylates prepared according to the invention, especially MMA prepared according to the invention, lead to particularly colour-free end products. This is the case, for example in polymerization processes which often subject products to degassing and recycle these recyclates obtained in the degassing into the polymerization in order for them to be used in a further polymerization step. This can result in the enrichment of by-products, in particular by-products of relatively low vapour pressure, during the process. This enrichment, in particular of dimethoxyisobutene (DMIB) and methyl isobutyrate results in later batches in a further increasing yellow discolouration of the polymer. Thus after a number of recyclates, portions of the recyclate must be discarded in order to deplete the recyclate circuit with respect to these by-products. This in turn leads to a reduction in the overall polymer yield. The process according to the invention now makes it possible, surprisingly, to perform markedly more batches with recycling and reuse of the recyclate and thus to achieve an appreciable increase in the overall polymer yield.

Surprisingly, it has furthermore also been found that with the process according to the invention not only is the DMIB content reduced, but the content of undesired methyl isobutyrate in the end product is also reduced.

A surprisingly identified negative effect exerted by DMIB in an alkyl methacrylate resin and descendant products produced therefrom is not only the yellow discolouration but also a reduced thermal stability of the polymer produced from the alkyl methacrylate. This is attributable to a more severe polymer chain degradation during thermal processing and takes effect in particular during processing to afford a molding and during workup of a polymer syrup. A further advantage of the present invention is thus that an alkyl methacrylate prepared according to the invention does not exhibit these disadvantages with respect to the polymers produced therefrom.

In addition to the specified process, novel alkyl methacrylates which may be obtained for example as a product from the process steps a to e of the invention form part of the subject matter of the present invention. Thus these novel alkyl methacrylates have the feature that the alkyl methacrylate necessarily comprises DMIB as a constituent. The alkyl methacrylate generally also comprises methyl isobutyrate.

These alkyl methacrylates are in particular those preparable by means of a very advantageous process which proceeds from a C2 basis instead of a C3 or C4 basis as the basic synthesis unit of methacrylate synthesis. What is novel about this alkyl methacrylate in particular is that, compared to the materials described in the prior art, while said alkyl methacrylate does comprise DMIB, the latter is present in a not previously known content of less than 90 ppm, preferably less than 50 ppm, very particularly preferably less than 20 ppm. In particular, contents of less than 90 ppm are particularly suitable for producing methacrylate resins without visible yellow discolouration.

The alkyl methacrylate according to the invention also preferably further comprises a methyl isobutyrate content of less than 250 ppm, particularly preferably less than 200 ppm and especially preferably less than 170 ppm.

LIST OF DESIGNATIONS

1—reactor II for the direct oxidative esterification of MAL and methanol to MMA
2—optional feed of fresh MAL; MAL may optionally also be supplied directly into 1
3—possible feed of sulfuric acid
4—feed stream to distillation column I
5—distillation column I for recycling MAL and methanol
6—recycle stream/distillate stream from 5 with MAL and methanol to 1 (reactor II)
7—possible feed of sulfuric acid and water
8—bottom stream departing from 5
9—optional reactor III for cleaving the acetal
10—possible feed of sulfuric acid and water
11—stream from reactor III into phase separator I
12—optional phase separator I
13—stream departing from phase separator I—aqueous phase (salt-rich)
14—bottom stream of distillation column IV
15—distillation column IV inter alia for recovering further methanol
16—distillate stream of distillation column IV—may optionally be recycled to reactor II or to 5 or to 6
17—aqueous bottom stream of extraction column I for feeding into distillation column IV
18—stream departing from phase separator I—organic phase (MMA-rich)
19—extraction column I inter alia for cleaving DMIB (methacrolein dimethyl acetal)
20—addition of extraction water to the top of extraction column I. Proportions of extraction water may come from 14
21—crude MMA, top stream departing from extraction column I, is sent to distillation column II

EXAMPLES

Example 1—Cleavage of the Acetal

The direct oxidative esterification of methacrolein and methanol to MMA was performed in a stirred tank over an Au-cobalt oxide@SiO2-Al2O3-MgO catalyst (see WO2017084969A1) at 80° C., 5 bar absolute, pH=7 and a molar ratio of methanol to methacrolein of 4 to 1 at the reactor inlet.

The reaction mixture obtained was sent together with the fresh methacrolein to a distillation column (dist. column I); the pressure of the column was 1000 mbar absolute, the reflux ratio was 1.00 and the bottom temperature was on average 73° C. The feed to the column was on average nearly 2800 g/h and the bottom output was approx. 1180 g/h.

The relevant constituent concentrations of the reaction product (RKP) and of the bottoms of distillation column I were:

|  | MAL | Acetal | $H_2O$ |
| --- | --- | --- | --- |
| RKP | 8.1 | 0.05 | 6.2 |
| Bottoms | 0.08 | 0.12 | 12.4 |

All figures in % by weight

The bottom output in a small acid-resistant stirred tank was continuously admixed with an aqueous sulfuric acid solution so that the pH was 2 and the ratio of bottoms to water feed was 0.77 (weight basis). The biphasic mixture was subjected to turbulent mixing in the stirred tank at 40° C. with an average residence time of 5 minutes. The biphasic mixture was then phase separated at 40° C. and both phases were analysed. The stream of organic phase was on average 773 g/h and the stream of aqueous phase was on average 1622 g/h.

The relevant constituent concentrations of the phases were:

|  | MAL | Acetal | $H_2O$ |
| --- | --- | --- | --- |
| Organics | 0.16 | 0.006 | 2.9 |
| Aqueous | 0.01 | n.d. | 83.0 |

All figures in % by weight
n.d. = not detectable The detection limit is below 5 ppm using GC-FID In addition, the MMA content in the organic phase of the phase separator was analysed and showed an (absolute) decrease of 0.4%, while the content of methacrylic acid in total rose by 0.3% (absolute). "In total" means the increase in methacrylic acid in the organic phase and also in the aqueous phase of the phase separator, the content being determined by means of HPLC, in order to exclude low results due to remaining methacrylic acid.

The organic phase was then sent into the bottom of an extraction column, the extraction being performed as a stirred cell extraction in countercurrent mode. The extraction parameters were analogous to the preceding reactor, 40° C. and the pH was 2. The ratio of organics to extraction water was 3.9 (weight basis). The stream of crude MMA, corresponding to the organics at the top of the extraction column, was on average 770 g/h.

The relevant constituent concentrations of the organics at the top of the extraction column (also called crude MMA) were:

|  | MAL | Acetal | $H_2O$ |
| --- | --- | --- | --- |
| Crude MMA | 0.40 | n.d. | 2.6 |

All figures in % by weight
n.d. = not detectable The detection limit is below 5 ppm using GC-FID The extraction water used was distilled water. It will be noted that the aqueous phase of the phase separator and the aqueous phase of the extraction may optionally be sent together into a second distillation column in order to remove the remaining organics there by distillation. The sulfuric acid-containing bottom product obtained in this distillation column can be used at least in portions for the acidification in the stirred tank and as extraction water, which can reduce the requirement for fresh water and fresh sulfuric acid in the process.

On the basis of the analyses and flows, the following conversions may be calculated:

Conversion of the acetal cleavage in the stirred tank=96.5%

Conversion of the acetal cleavage in the extraction column=3.5%

Total conversion of the acetal cleavage=>99.99%

On the basis of the analyses and flows, the release of methacrolein can additionally be determined:

|  | Flow [g/h] | MAL [% by wt.] | MAL [g] |
|---|---|---|---|
| Bottoms dist. column I | 1180 | 0.08 | 0.9 |
| Organics phase separator | 773 | 0.16 | 1.2 |
| Crude MMA | 770 | 0.40 | 3.1 |

It can therefore be seen that the proportion and the amount of methacrolein increase as a result of the acetal cleavage and—at least in proportions—can be recycled into the direct oxidative esterification.

The crude MMA obtained was purified by means of a high boiler distillation column and a low boiler distillation column and stabilized in a final purifying distillation column to a commercial quality. The MMA quality obtained is shown in Table 1.

Example 2—Variation of the pH for the Acetal Cleavage

Example 2a—pH=3

The experiment was conducted analogously to Example 1, but the pH for the acetal cleavage was 3. The following conversions were achieved:

Conversion of the acetal cleavage in the stirred tank=73.2%

Conversion of the acetal cleavage in the extraction column=24.7%

Total conversion of the acetal cleavage=97.9%

Example 2b—pH=4

The experiment was conducted analogously to Example 1, but the pH for the acetal cleavage was 4. The following conversions were achieved:

Conversion of the acetal cleavage in the stirred tank=31.0%

Conversion of the acetal cleavage in the extraction column=59.4%

Total conversion of the acetal cleavage=90.4%

Example 2c—pH=5

The experiment was conducted analogously to Example 1, but the pH for the acetal cleavage was 5. The following conversions were achieved:

Conversion of the acetal cleavage in the stirred tank=9.7%

Conversion of the acetal cleavage in the extraction column=32.5%

Total conversion of the acetal cleavage=42.2%

Examples 1 and 2 have shown that at low pH the majority of the acetal cleavage takes place in the stirred tank, and thus acetal contents of less than 20 ppm can be achieved. As the pH increases, the proportion of conversion shifts towards the extraction, and overall it is no longer possible to achieve conversions of more than 97%, which would be necessary for a pure MMA with acetal contents of less than 20 ppm.

The further MMA workup is effected analogously to Example 1 and the results are summarized in Table 1:

TABLE 1

Overview of pure MMA quality

| Example | pH | MMA - % by wt. | Acetal - ppm | Methyl isobutyrate - ppm |
|---|---|---|---|---|
| 1 | 2 | 99.98 | 3 | 120 |
| 2a | 3 | 99.98 | 15 | 138 |
| 2b | 4 | 99.97 | 76 | 145 |
| 2c | 5 | 99.91 | 636 | 170 |

It can be seen that as the pH increases and hence the conversion drops in the acetal cleavage there is an accumulation of acetal and methyl isobutyrate in the pure MMA—as a result of which in the later processing the yellowness index in the polymer rises and hence the optical quality falls.

Example 3—Addition of the Acid into the Bottom of Distillation Column I

The aqueous sulfuric acid was fed into the bottom of distillation column I at the same mass flow rate as in Example 1, resulting in a pH of 2. Mixing resulted from the heat-induced circulation in the column bottoms. The residence time in the column bottom was approximately 10 min. The stirred tank was dispensed with and the column bottoms were sent directly into the phase separation. The achieved conversion of acetal cleavage in the column bottom was greater than 99%; however, on account of the prolonged residence time and the relatively high temperature, secondary reactions/polymerization formation occurred, as a result of which a brown-coloured rag phase between the organic and the aqueous phase formed in the phase separation, disrupting the fill level control of the phase separation and causing fluctuations in the mass flow rate into the extraction. This results in a fluctuating MMA content in the crude MMA and aqueous product of the extraction, as a result of which the general plant operation became more sensitive and the final pure MMA quality fluctuated.

Therefore, while it is in principle possible to conduct the acetal cleavage in the column bottom with sulfuric acid, this means that the following phase separation/extraction for long-term operation must be equipped with a technical means for removing the rag phase in order to enable stable operation; additional costs moreover result from this.

Example 4—Tubular Reactor Instead of Stirred Tank for Acetal Cleavage

A tubular reactor, with a length of 60 m and an internal diameter of 4 mm and three static mixers distributed uniformly over the reactor, was supplied with a stream of the bottom output from the first distillation column (see Example 1 for the composition) and of an aqueous sulfuric acid solution such that the residence time in the reactor was 83 seconds. The ratio of organics to aqueous sulfuric acid was 0.71 (weight basis) and the pH was 3. The tubular reactor was operated at 80° C. by means of preheating of the feed streams and jacket heating.

Downstream of the tubular reactor, the reaction mixture was cooled down to 40° C. and the phases were separated analogously to Example 1. The conversion of the acetal cleavage was determined by GC analysis and was 96.1%, and therefore higher than in the stirred tank. This example shows that as a result of improved mixing and higher reaction temperature the space-time yield of the acetal cleavage can be increased and at the same time the consumption of sulfuric acid is reduced (tubular reactor=1.37 mol DMIB/kg $H_2SO_4 \times hr$ vs. stirred tank=1.2 mol DMIB/kg $H_2SO_4 \times hr$). As a result of the reduced pH during the cleavage, the requirement for acid resistance of the reactor material used also falls, which brings technical and economic advantages for the reaction step and the process.

Example 5—Acetal Cleavage in Stirred Tank at Elevated Temperature

The experiment was conducted analogously to Example 1, but the temperature was raised from 40 to 80° C. The following conversions were achieved:
  Conversion of the acetal cleavage in the stirred tank=98.9%
  Conversion of the acetal cleavage in the extraction column=1.0%
  Total conversion of the acetal cleavage=>99.99%

However, the MMA content in the organic phase of the phase separator fell by 2.8%. At the same time, the content of methacrylic acid in the aqueous phase and organic phase of the phase separator rose in total by 2.3%. "In total" means the increase in methacrylic acid in the organic phase and also in the aqueous phase of the phase separator, the content being determined by means of HPLC, in order to exclude low results due to remaining methacrylic acid.

This suggests that the rise in temperature results in the MMA being hydrolysed to methacrylic acid.

Example 6—Acetal Cleavage in Stirred Tank at Elevated Temperature and Extended Residence Time The experiment was conducted analogously to Example 1, but the temperature was raised from 40 to 80° C. and the residence time was doubled from nearly 5 to nearly 10 minutes. The following conversions were achieved:
  Conversion of the acetal cleavage in the stirred tank=99.8%
  Conversion of the acetal cleavage in the extraction column=0.1%
  Total conversion of the acetal cleavage=>99.99%

However, the MMA content in the organic phase of the phase separator fell by 5.4%. At the same time, the content of methacrylic acid in the aqueous phase and organic phase of the phase separator rose in total by 4.5%. "In total" means the increase in methacrylic acid in the organic phase and also in the aqueous phase of the phase separator, the content being determined by means of HPLC, in order to exclude low results due to remaining methacrylic acid. This suggests that the rise in temperature results in the MMA being hydrolysed to methacrylic acid.

Examples 5 and 6 show that at elevated temperatures and/or extended residence times there is not only increased conversion of the acetal cleavage, but additionally a considerable hydrolysis of MMA, as a result of which material of value is lost.

Example 7—Acetal Cleavage in Stirred Tank with Varied pH

The experiment was conducted analogously to Example 1, but the pH for the acetal cleavage was 1. The following conversions were achieved:
  Conversion of the acetal cleavage in the stirred tank=99.8%
  Conversion of the acetal cleavage in the extraction column=0.1%
  Total conversion of the acetal cleavage=>99.99%

However, the MMA content in the organic phase of the phase separator fell by 2.5%. At the same time, the content of methacrylic acid in the aqueous phase and organic phase of the phase separator rose in total by 2.1%. "In total" means the increase in methacrylic acid in the organic phase and also in the aqueous phase of the phase separator, the content being determined by means of HPLC, in order to exclude low results due to remaining methacrylic acid. This suggests that the rise in temperature results in the MMA being hydrolysed to methacrylic acid.

Example 7 shows that a sufficiently high conversion in the acetal cleavage may also be achieved without the extraction, but at the cost of MMA loss and hence a loss of material of value or process product.

Nevertheless. Examples 5 to 7 are examples according to the invention, since here compared to the prior art in each case the proportion of hydrolysed MMA is always lower and at the same time the acetals are cleaved efficiently.

The invention claimed is:

1. A process for preparing alkyl methacrylates, comprising:
  a) preparing methacrolein in a reactor I,
  b) oxidatively esterifying the methacrolein in the presence of an alcohol, oxygen, and a heterogeneous noble metal-containing catalyst in at least one reactor II,
  c) distilling a reactor output from the at least one reactor II in a distillation column I for separation of the methacrolein and portions of the methanol,
  d) optionally, pretreating a bottom output from c), comprising
    i) adding an acid to change a pH of the bottom output,
    ii) adding water to obtain a biphasic mixture, and
    iii) reactively treating at least a portion of the biphasic mixture from ii), and
  e) extracting the bottom output from distillation column I from c) or an organic phase of the bottom output from distillation column I from d), in an extraction I,
  wherein an amount of the methacrolein in the organic phase from extraction I is greater than that in the bottom output from distillation column I, and
  wherein there is produced an alkyl methacrylate composition comprising methacrolein dimethyl acetal (DMIB), and which has a DMIB content of less than 90 ppm.

2. The process according to claim 1, wherein e) is an extraction of the bottom output from distillation column I from the extraction I, wherein extraction I and optionally distillation column I are acid-resistant, wherein an organic and/or a mineral acid is mixed with the reactor output from the at least one reactor II, and is passed into the distillation column I and/or the extraction I, wherein the reactor output has an average residence time in distillation column I of between 1 and 30 min at a temperature of between 30 and 100° C., and wherein in extraction I, the bottom output transferred from distillation column I with additionally transferred acid resides in the extraction I at a temperature of between 10 and 100° C. for 1 to 20 min.

3. The process according to claim 1, wherein a reaction in the at least one reactor II is effected at a water content of between 0.1% and 10% by weight and a pH of between 5 and 8.

4. The process according to claim 1, wherein a) in reactor I involves a reaction of propanal with formaldehyde in the presence of at least one acid and optionally an amine, and wherein the alcohol in b) is methanol and the alkyl methacrylate is methyl methacrylate (MMA).

5. The process according to claim 1, wherein in c), methacrolein dimethyl acetal is cleaved with water into methacrolein and methanol, which in distillation column I together with remaining reactants of b), are largely removed overhead or in a side stream of the distillation column I and are recycled into the at least one reactor II.

6. The process according to claim 1, wherein in c), sulfuric acid is passed into the distillation column I and optionally, additionally in e) into the extraction I.

7. The process according to claim 1, wherein additional water is introduced into the bottom output of distillation column I, and wherein the distillation is effected at a bottom temperature of between 50 and 100° C.

8. The process according to claim 1, wherein the extraction I involves a mixer-settler, and wherein an extractant used is water, aqueous sulfuric acid, or a bottom stream from an additional distillation column IV.

9. The process according to claim 1, wherein the acid is added to the bottom output departing from the bottom of distillation column I.

10. The process according to claim 1, wherein e) is followed by isolation and purification stages, which comprise at least one optional phase separator, at least one high boiler column, and at least one low boiler column.

11. The process according to claim 10, wherein d) is present and wherein in d) in the extraction I, the bottom output from distillation column I is separated into the organic phase containing MMA and a polar phase containing the acid and salts thereof, and wherein the organic phase is subsequently passed into a distillation column II.

12. The process according to claim 11, wherein the distillation column II is of acid-resistant design, and wherein a further acid is introduced into a bottom and/or a feed of distillation column 11.

13. The process according to claim 11, wherein the distillation column II is a distillation column for separating low-boiling constituents from the organic phase, into a bottom and/or a feed of which a further acid is introduced, and wherein bottoms of distillation column II are passed into an acid-resistant distillation column III for separating high-boiling constituents from an MMA phase.

14. The process according to claim 1, wherein the acid added has a pKa value which is 1 less than that of methacrylic acid.

15. The process according to claim 11, wherein the distillation column II is a distillation column for separating high-boiling constituents from the organic phase.

16. The process according to claim 12, wherein the further acid is sulfuric acid.

17. The process according to claim 13, wherein the further acid is sulfuric acid.

18. The process according to claim 1, wherein the composition comprises methyl isobutyrate, and has a methyl isobutyrate content of less than 240 ppm.

19. The process according to claim 1, wherein d) is present.

* * * * *